United States Patent [19]

Sevrin et al.

[11] Patent Number: 5,665,733

[45] Date of Patent: Sep. 9, 1997

[54] 3-PHENYLISOQUINOL-1(2H)-ONE DERIVATIVES THEIR PREPARATION AND THEIR THERAPEUTIC APPLICATION

[75] Inventors: Mireille Sevrin, Paris; Benoit Marabout, Chilly Mazarin; Jacques Froissant, Morée; Catherine Guinot, Paris, all of France

[73] Assignee: Synthelabo, Le Plessis Robinson, France

[21] Appl. No.: 579,677

[22] Filed: Dec. 28, 1995

[30] Foreign Application Priority Data

Dec. 29, 1994 [FR] France .................. 94 15837

[51] Int. Cl.$^6$ .................................. A61K 31/47
[52] U.S. Cl. ............................ 514/309; 546/141
[58] Field of Search ................ 546/141; 514/309

[56] References Cited

PUBLICATIONS

Coston, A et al 'Aortic Occlusion by a Balloon Catheter: A Method to Induce Hind Limb Rigidity in Rats' Phys. and Behavior, vol. 30, pp. 967–969 (1983).

*Primary Examiner*—Amelia Owens
*Attorney, Agent, or Firm*—Foley & Lardner

[57] ABSTRACT

A compound of formula (I)

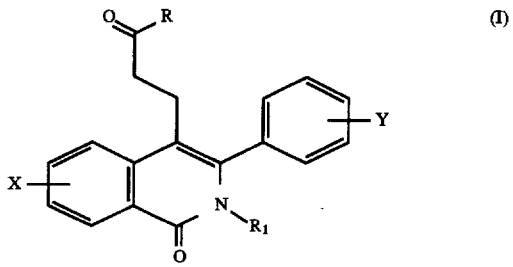

in which

X represents a hydrogen atom, a halogen atom, a trifluoromethyl group, a $C_1$–$C_3$ alkyl group or a $C_1$–$C_3$ alkoxy group in which case two such alkoxy groups X can be present, Y represents a hydrogen atom, a halogen atom, a $C_1$–$C_3$ alkyl group or a $C_1$–$C_3$ alkoxy group, $R_1$ represents $C_1$–$C_4$ alkyl group, and R represents a hydroxyl group, a methoxy group, an ethoxy group or a group of formula $NR_2R_3$ in which $R_2$ and $R_3$ each independently represents a hydrogen atom or a $C_1$–$C_4$ alkyl group, or a pharmaceutically acceptable addition salt thereof, processes for their preparation and their therapeutic application.

7 Claims, No Drawings

3-PHENYLISOQUINOL-1(2H)-ONE DERIVATIVES THEIR PREPARATION AND THEIR THERAPEUTIC APPLICATION

The present invention relates to 3-phenylisoquinol-1(2H)-one derivatives, their preparation and their therapeutic application.

The present invention provides a compound of formula (I)

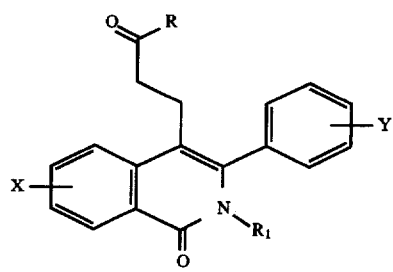

in which

X represents a hydrogen atom, a halogen atom, a trifluoromethyl group, a $C_1$–$C_3$ alkyl group or a $C_1$–$C_3$ alkoxy group in which case two such alkoxy groups X can be present, Y represents a hydrogen atom, a halogen atom, a $C_1$–$C_3$ alkyl group or a $C_1$–$C_3$ alkoxy group, $R_1$ represents a $C_1$–$C_4$ alkyl group, and R represents a hydroxyl group, a methoxy group, an ethoxy group or a group of formula $NR_2R_3$ in which $R_2$ and $R_3$ each independently represents a hydrogen atom or a $C_1$–$C_4$ alkyl group, or a pharmaceutically acceptable addition salt thereof.

The preferred compounds of the invention are those in which $R_1$ represents a methyl group and R represents a methylamino group.

In accordance with the invention, the compounds of formula (I) can be prepared by a process illustrated in general by the following scheme.

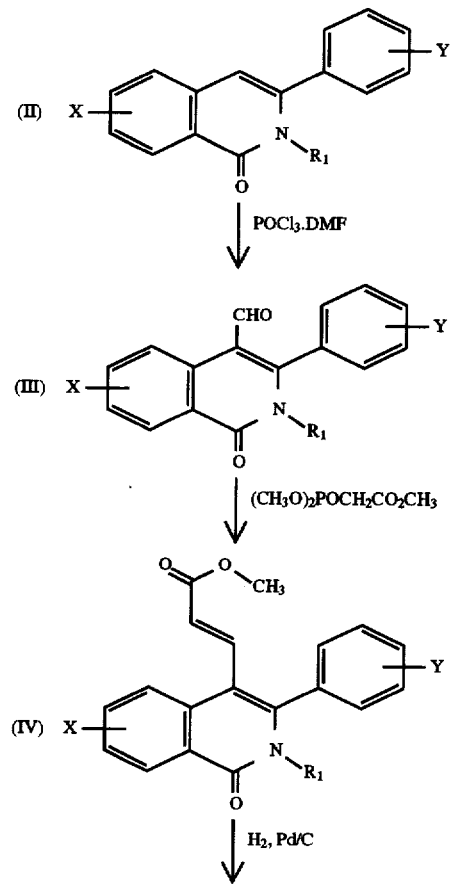

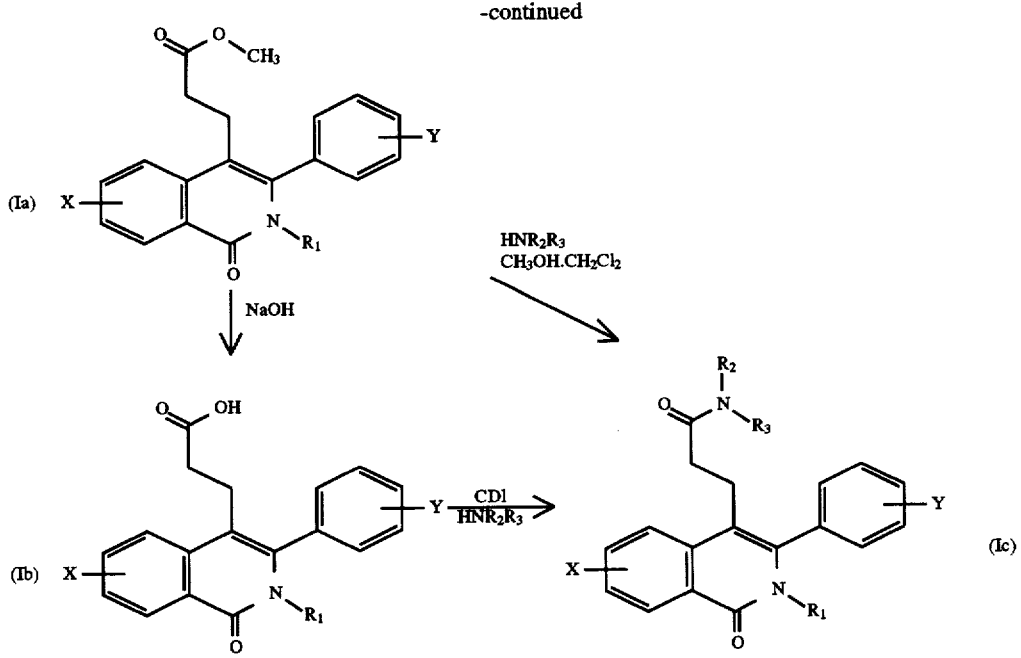

A 3-phenylisoquinol-2(2 H)-one of formula (II), in which X, Y and $R_1$ are as defined above, is treated with phosphorus oxychloride generally in a solvent such as N,N-dimethylformamide, at a temperature of 80° to 120° C., to obtain, after hydrolysis, an aldehyde of formula (III), which is then treated with methyl (dimethoxyphosphinyl)acetate, generally in a solvent such as tetrahydrofuran, at a temperature of 20° to 67° C., to obtain a methyl ester of formula (IV), which is hydrogenated, for example in the presence of palladium-on-charcoal, to obtain an ester of formula (Ia), which corresponds to a compound of formula (I) in which R represents a methoxy group.

If a compound of formula (I) in which R represents a hydroxyl group is desired, the ester of general formula (Ia) is hydrolysed generally in a basic medium, in a solvent such as ethanol or methanol, at a temperature of 60° to 80° C., to obtain a compound of formula (Ib) and, if a compound of formula (I) in which R represents a group of formula $NR_2R_3$ is desired, either the ester of formula (Ia) is treated with an amine of formula $HNR_2R_3$, generally at room temperature and in a solvent such as a mixture of methanol and dichloromethane, or the acid of formula (Ia) is treated with this amine via the intermediacy of the imidazolide prepared in situ using N,N'-carbonyldiimidazole.

To prepare a compound of formula (I) in which R represents an ethoxy group, an acid of formula (Ib) is reacted with thionyl chloride in ethanol, generally at a temperature of 20° to 65° C.

If desired, the compound of formula (I) is converted into an addition salt thereof by known methods.

The starting compounds, of formula (II), are known and can be prepared by methods analogous to those described in Synthesis (1982), 329–330, Synthesis (1980), 10, 845–847, CA 79(15), 91351k and CA 76(1), 3666b. The intermediates of formulae (III) and (IV) are known and described in EP-A-0,424,929.

The Examples which follow illustrate the preparation of a number of compounds of the invention. The elemental microanalyses and the I.R. and N.M.R. spectra confirm the structures of the compounds obtained. The numbers indicated between brackets in the titles of the examples correspond to those in the first column of Table 1 given later.

EXAMPLE 1 (COMPOUND NO. 2)

Methyl 2-methyl-1-oxo-3-phenyl-1,2-dihydroisoquinoline-4-propanoate.

1.1. 2-Methyl-1-oxo-3-phenyl-1,2-dihydroisoquinoline-4-carboxaldehyde.

80 ml of dry N, N-dimethylformamide are cooled to 0° C., under an argon atmosphere, 6.8 ml (71.7 mmol) of phosphorus oxychloride are then added dropwise and the mixture is stirred at room temperature for 1 h. 5 g (21.25 mmol) of 2-methyl-3-phenylisoquinol-1(2 H)-one, in solution in 1,2-dichloroethane, are added, the mixture is gradually heated to 120° C. and is maintained at this temperature for 4 h. It is cooled to room temperature, the solvent is evaporated under reduced pressure, 200 ml of diethyl ether and ice are added to the residue, 1N sodium hydroxide is added, the organic phase is separated and the aqueous phase is extracted with 200 ml of dichloromethane. The two organic phases are combined, dried over sodium sulphate and filtered and the solvents are evaporated under reduced pressure. The product obtained is purified by chromatography on a column of silica gel, elution being carried out with a mixture of cyclohexane and dichloromethane ranging from 80/20 to 50/50 and then with a mixture of dichloromethane and ethyl acetate ranging from 100/0 to 70/30. After recrystallizing from cyclohexane, 3.93 g (14.93 mmol) of white solid are obtained. Melting point: 138°–141° C.

1.2. methyl (E)-3-(2-methyl-1-oxo-3-phenyl-1,2-dihydroisoquinol-4-yl)prop-2-enoate. 0.9 g of sodium hydride as a 60% suspension in oil (22.5 mmol) is introduced into a 500 ml round-bottomed flask placed under an argon atmosphere, washed with pentane and suspended in 150 ml of dry tetrahydrofuran. The mixture is cooled to 0° C. with an ice bath, 3.4 g (18.7 mmol) of methyl (dimethoxyphosphinyl)acetate, in solution in 10 ml of tetrahydrofuran, are added dropwise and the mixture is stirred for 30 min at room temperature. 4 g (15.2 mmol) of 2-methyl-1-oxo-3-phenyl-1,2-dihydroisoquinoline-4- carboxaldehyde are then added and The mixture is gradually heated to reflux of the tetrahydrofuran and maintained at this temperature for 6 h. The mixture is cooled to 0° C. in an ice bath, a few drops of methanol are added in order to neutralize the excess hydride and the solvents are evaporated under reduced pressure. 250 ml of dichloromethane and ice-cold water are added to the residue, the organic phase is separated, washed with water, dried over sodium sulphate and filtered, the solvent is evaporated under reduced pressure and the residue is purified by chromatography on a column of silica gel, elution being carried out with a mixture of dichloromethane and ethyl acetate ranging from 100/0 to 70/30. The product is recrystallized from a mixture of cyclohexane and dichloromethane in order to obtain 3.84 g (12.02 mmol) of white solid. Melting point: 184°–185° C.

1.3. Methyl 2-methyl-1-oxo-3-phenyl-1,2-dihydroisoquinoline-4-propanoate.

0.25 g of 5% palladium-on-charcoal is added to a solution of 3.8 g (11.9 mmol) of methyl (E)-3-(2-methyl-1-oxo-3-phenyl-1,2-dihydroisoquinol-4-yl)prop-2-enoate in 100 ml of acetic acid and the suspension is subjected to hydrogenation in a Parr apparatus under pressure of approximately 0.3 MPa for 1 h at room temperature and then for 3 h at approximately 50° C. The catalyst is removed by filtering, the filtrate is concentrated under reduced pressure, ice-cold water, 200 ml of dichloromethane and 100 ml of 1N sodium hydroxide are added to the residue, the organic phase is separated, washed with water and dried over sodium sulphate and the solvent is evaporated under reduced pressure. The crude product is purified by chromatography on a column of silica gel, elution being carried out with a mixture of dichloromethane and ethyl acetate ranging from 100/0 to 70/30. After recrystallizing from a mixture of cyclohexane and dichloromethane, 2.69 g (8.37 mmol) of white solid are obtained. Melting point: 134°–135° C.

EXAMPLE 2 (COMPOUND NO. 1)

2-Methyl-1-oxo-3-phenyl-1,2-dihydroisoquinoline-4-propanoic acid.

1.2 g (3.7 mmol) of methyl 2-methyl-1-oxo-3-phenyl-1,2-dihydroisoquinoline-4-propanoate are dissolved in 80 ml of methanol in a 250 ml round-bottomed flask, 0.25 g (6.25 mmol) of sodium hydroxide pellets and 1 ml of water are added and then the mixture is stirred at room temperature for 1 h and at reflux for 2 h. The mixture is cooled, the solvent is evaporated under reduced pressure, the residue is taken up in 50 ml of water and 50 ml of diethyl ether, and 36% hydrochloric acid is added dropwise. The insoluble material is collected by filtering, is washed with water and is dried. 0.91 g (2.96 mmol) of white solid is obtained. Melting point: 138°–140° C.

EXAMPLE 3 (COMPOUND NO. 4)

N,2-Dimethyl-1-oxo-3-phenyl-1,2-dihydroisoquinoline-4-propanamide.

A stream of gaseous methylamine is passed into a 250 ml round-bottomed flask containing a solution of 1.25 g (3.85 mmol) of methyl 2-methyl-1-oxo-3-phenyl-1,2-dihydroisoquinoline-4-propanoate in 20 ml of dichloromethane and 80 ml of methanol until saturation and the mixture is left stirring at room temperature for 3 days. The solvents are evaporated under reduced pressure and the residue is purified by chromatography on a column of silica gel, elution being carried out with a mixture of dichloromethane and ethyl acetate ranging from 100/0 to 80/20 and then with a 95/5 mixture of dichloromethane and methanol. After recrystallizing from acetonitrile, 0.85 g (2.65 mmol) of white crystalline solid is obtained. Melting point: 185°–186° C.

EXAMPLE 4 (COMPOUND NO. 23)

N,N,2-Trimethyl-1-oxo-3-phenyl-1,2-dihydroisoquinoline-4-propanamide.

A suspension of 0.9 g (2.93 mmol) of 2-methyl-1-oxo-3-phenyl-1,2-dihydroisoquinoline-4-propanoic acid in 150 ml of dichloromethane is prepared in a 500 ml round-bottomed flask placed under an argon atmosphere, 0.7 g (4.3 mmol) of N,N'-carbonyldiimidazole is added, the mixture is stirred at room temperature for 2 h, is saturated for 1 min with gaseous dimethylamine and stirring is continued for 12 h. The solvent is evaporated under reduced pressure, the residue is taken up in 200 ml of dichloromethane, 100 ml of water and 1M hydrochloric acid, the organic phase is separated, washed with water, dried over sodium sulphate and filtered and the solvent is evaporated under reduced pressure. The residue is purified by chromatography on a column of silica gel, elution being carried out with a mixture of dichloromethane and ethyl acetate ranging from 100/0 to 70/30 and then with a 95/5 mixture of dichloromethane and methanol. After recrystallizing from a mixture of dichloromethane, methanol and acetonitrile, 0.72 g (2.15 mmol) of white solid is obtained. Melting point: 165.5°–166° C.

EXAMPLE 5 (COMPOUND NO. 10)

N,2-Dimethyl-7-chloro-1-oxo-3-phenyl-1,2-dihydroisoquinoline-4-propanamide.

5.1. 7-Chloro-2-methyl-1-oxo-3-phenyl-1,2-dihydroisoquinoline-4-carboxaldehyde 100 ml of dry N,N-dimethylformamide are cooled to 0° C., under an argon atmosphere, 12 ml (128 mmol) of phosphorus oxychloride are added dropwise and the mixture is stirred at room temperature for 1 h. 13.7 g (51 mmol) of 7-chloro-2-methyl-3-phenylisoquinol-1(2 H)-one are added and the mixture is gradually heated to 110° C. and is maintained at this temperature for 4 h. It is cooled to room temperature, the solvent is evaporated under reduced pressure, 200 ml of diethyl ether and ice are added to the residue, 1N sodium hydroxide is added, the organic phase is separated and the aqueous phase is extracted with 200 ml of dichloromethane. The two organic phases are combined, dried over sodium sulphate and filtered and the solvents are evaporated under reduced pressure. The residue is purified by chromatography on a column of silica gel, elution being carried out with a mixture of cyclohexane and dichloromethane ranging from 80/20 to 50/50 and then with a mixture of dichloromethane and ethyl acetate ranging from 100/0 to 70/30. After recrystallizing from cyclohexane, 7.68 g (26 mmol) of white solid are obtained. Melting point: 172°–173° C.

5.2. Methyl (E)-3-(7-chloro-2-methyl-1-oxo-3-phenyl-1,2-dihydroisoquinol-4-yl)prop-2-enoate. 1.3 g of sodium hydride as a 60% suspension in oil (32.5 mmol) are introduced into a 500 ml round-bottomed flask placed under an argon atmosphere, washed with pentane and suspended in 200 ml of dry tetrahydrofuran. The mixture is cooled to 0° C. with an ice bath, 4.6 ml (28 mmol) of methyl (dimethoxyphosphinyl)acetate, in solution in 10 ml of tetrahydrofuran, are added dropwise and the mixture is stirred for 30 min at room temperature. 7.68 g (26 mmol) of 7-chloro-2-methyl-1-oxo-3-phenyl-1,2-dihydroisoquinoline-4-carboxaldehyde are then added, the mixture is gradually heated to reflux of the tetrahydrofuran and is maintained at this temperature for 3 h. It is cooled to 0° C. with an ice bath, a few drops of methanol are added in order to neutralize the excess hydride and the solvents are evaporated under reduced pressure. 250 ml of dichloromethane and ice-cold water are added to the residue, the organic phase is separated, washed with water, dried over sodium sulphate and filtered, the solvent is evaporated under reduced pressure and the residue is purified by chromatography on a column of silica gel, elution being carried out with a mixture of dichloromethane and ethyl acetate ranging from 100/0 to 70/30. The product is recrystallized from a mixture of cyclohexane and dichloromethane in order to obtain 8.35 g (23.6 mmol) of white solid. Melting point: 185°–188° C.

5.3. Methyl 7-chloro-2-methyl-1-oxo-3-phenyl-1,2-dihydroisoquinoline-4-propanoate.

0.8 g of platinum oxide is added to a solution of 8.35 g (23.6 mmol) of methyl (E)-3-(7-chloro-2-methyl-1-oxo-3-phenyl-1,2-dihydroisoquinol-4-yl)prop-2-enoate in 150 ml of ethyl acetate and the suspension is subjected to hydrogenation in a Parr apparatus under a pressure of approximately 0.3 MPa for 5 h at room temperature. The catalyst is removed by filtering and the filtrate is concentrated under reduced pressure. The crude product is purified by chromatography on a column of silica gel, elution being carried out with a mixture of cyclohexane and dichloromethane ranging from 50/50 to 0/100 and then with a mixture of dichloromethane and ethyl acetate ranging from 100/0 to 90/10. After evaporating the solvents under reduced pressure, the residue is taken up in cyclohexane in order to obtain 4.73 g (13.3 mmol) of white solid. Melting point: 143°–144° C.

5.4. N,2-Dimethyl-7-chloro-1-oxo-3-phenyl-1,2-dihydroisoquinoline-4-propanamide.

A stream of gaseous methylamine is passed into a 250 ml round-bottomed flask containing a solution of 1.7 g (4.78 mmol) of methyl7-chloro-2-methyl-1-oxo-3-phenyl-1,2-dihydroisoquinoline-4-propanoate in 20 ml of dichloromethane and 80 ml of methanol until saturation and the mixture is left stirring at room temperature for 4 days. The solvents are evaporated under reduced pressure and the residue is purified by chromatography on a column of silica gel, elution being carried out with a mixture of dichloromethane and ethyl acetate ranging from 100/0 to 80/20 and then with a 95/5 mixture of dichloromethane and methanol. After recrystallizing from ethyl acetate, 1.36 g (3.83 mmol) of white solid are obtained. Melting point: 161°–162° C.

The chemical structures and the physical properties of a few compounds of general formula (I) are illustrated in the following table.

TABLE

| No. | X | Y | $R_1$ | R | M.p. (°C.) |
|---|---|---|---|---|---|
| 1 | H | H | $CH_3$ | OH | 138–140 |
| 2 | H | H | $CH_3$ | $OCH_3$ | 134–135 |
| 3 | H | H | $CH_3$ | $OCH_2CH_3$ | 109.5–111 |
| 4 | H | H | $CH_3$ | $NHCH_3$ | 185–186 |
| 5 | 5-$OCH_3$ | H | $CH_3$ | $NHCH_3$ | 178.5–180 |
| 6 | 6-$CH_3$ | H | $CH_3$ | $NHCH_3$ | 123–124 |
| 7 | 6-Cl | H | $CH_3$ | $NHCH_3$ | 170–171 |
| 8 | 6-$OCH_3$ | H | $CH_3$ | $NHCH_3$ | 182–183 |
| 9 | 7-$CH_3$ | H | $CH_3$ | $NHCH_3$ | 154.5–155.5 |
| 10 | 7-Cl | H | $CH_3$ | $NHCH_3$ | 161–162 |
| 11 | 7-Cl | H | $CH_3$ | $NH(CH_2)_3CH_3$ | 132–133 |
| 12 | 7-$OCH_3$ | H | $CH_3$ | $NHCH_3$ | 207–208 |
| 13 | 7-$CF_3$ | H | $CH_3$ | $NHCH_3$ | 172–174 |
| 14 | 8-$OCH_3$ | H | $CH_3$ | $NHCH_3$ | 171–173 |
| 15 | 6,7-$(OCH_3)_2$ | H | $CH_3$ | $NHCH_3$ | 255–256 |
| 16 | H | 3-$CH_3$ | $CH_3$ | $NHCH_3$ | 190.5–192 |
| 17 | H | 3-$OCH_3$ | $CH_3$ | $NHCH_3$ | 168.5–169.5 |
| 18 | H | 3-Cl | $CH_3$ | $NHCH_3$ | 193.5–194.5 |
| 19 | H | 4-F | $CH_3$ | $NHCH_3$ | 164–166 |
| 20 | H | 4-Cl | $CH_3$ | $NHCH_3$ | 224–224.5 |
| 21 | 7-$CH_3$ | 3-Cl | $CH_3$ | $NHCH_3$ | 175.5–176.5 |
| 22 | 7-$CH_3$ | 3-F | $CH_3$ | $NHCH_3$ | 165–166 |
| 23 | H | H | $CH_3$ | $N(CH_3)_2$ | 165.5–166 |
| 24 | 7-Cl | H | $CH_3$ | $N(CH_2CH_3)_2$ | 141.8–142.3 |
| 25 | H | H | $CH_2CH_3$ | OH | 298–303 |
| 26 | H | H | $CH_2CH_3$ | $NHCH_3$ | 152–153 |
| 27 | H | H | $CH_2CH_3$ | $N(CH_3)_2$ | 195–197 |
| 28 | H | H | $(CH_2)_2CH_3$ | $NHCH_3$ | 205.5–207.5 |

The compounds of the invention were subjected to pharmacological tests which demonstrated their advantage as substances having therapeutic activities.

Study of the membrane binding with respect to a population of ω receptors (benzodiazepine receptors) associated with GABA$_A$ receptors containing the α$_5$ subunit.

These receptors can be selectively labelled in rat hippocampus membranes incubated in the presence of [$^3$H] flumazenil and of 5 μM zolpidem (in order to mask the other ω-receptor subtypes).

The compounds formed the subject of an in vitro study as regards their affinity for these receptors labelled with [$^3$H] flumazenil.

The animals used are OFA (Iffa Credo) male rats weighing 200 to 250 g. After decapitation, the hippocampus is removed and is ground using an Ultra-Turrax™ or Polytron™ apparatus for 20 s at 9/10 of the maximum speed in 80 volumes of 50 mM Tris buffer at a pH adjusted to 7.4 with hydrochloric acid and containing 120 mM of sodium chloride and 5 mM of potassium chloride (5 mM).

The binding with [$^3$H] flumazenil (1 nM; specific activity: 80–87 Ci/mmol; Du Pont de Nemours/New England Nuclear) is determined by incubating 200 μl of membrane suspension in a final volume of 1 ml of buffer containing 5 μM of zolpidem and the test compound. After incubating for 45 min at 0° C., the membranes are recovered by filtration on Whatman GF/B™ filters which are washed twice with 5 ml of ice-cold buffer. The amount of radioactivity retained by the filter is measured by liquid scintigraphy.

The specific binding of [$^3$H] flumazenil is defined as the amount of radioactivity retained on the filters and capable of being inhibited by coincubation with 1 μM flunitrazepam.

For each concentration of test compound, the percentage of inhibition of the binding of [$^3$H] flumazenil, and then the IC$_{50}$ concentration, the concentration which inhibits 50% of the specific binding, are determined.

The compounds of the invention which are the most active in this test have an IC$_{50}$ of the order of 10 to 400 nM.

Study of the membrane bindings with respect to ω$_2$ receptors (type-II benzodiazepine receptors) associated with GABA$_A$ receptors containing mostly the α$_2$ and α$_3$ subunits.

The affinity of the compounds for the ω$_2$ receptors of the spinal cord was determined according to a variant of the method described by S. Z. Langer and S. Arbilla in *Fund. Clin. Pharmacol.* (1988), 2, 159–170, with the use of [$^3$H] flumazenil in place of [$^3$H] diazepam as radioligand.

The tissue of the spinal cord is homogenized for 60 s in 30 volumes of ice-cold buffer (50 mM of Tris/HCl, pH 7.4, 120 mM NaCl, 5 mM KCl) and then, after dilution to ⅓, the suspension is incubated with [$^3$H] flumazenil (specific activity: 78 Ci/mmol; New England Nuclear) at a concentration of 1 nM and with the compounds of the invention, at different concentrations, in a final volume of 525 μl. After incubating for 30 min at 0° C., the samples are filtered under vacuum on Whatman GF/B™ filters and they are washed immediately with ice-cold buffer. The specific binding of [$^3$H] flumazenil is determined in the presence of 1 μM unlabelled diazepam. The data are analysed according to the usual methods and the IC$_{50}$, the concentration which inhibits 50% of the binding of [$^3$H] flumazenil, is calculated.

The IC$_{50}$ values of the compounds of the invention lie, in this test, between 0.05 and 10 μM.

Study of the membrane bindings with respect to ω$_1$ receptors (type-I benzodiazepine receptors) associated with GABA$_A$ receptors containing the α$_1$ subunit.

The affinity of the compounds for the ω$_1$ receptors of the cerebellum was determined according to a variant of the method described by S. Z. Langer and S. Arbilla in *Fund. Clin. Pharmacol.* (1988), 2, 159–170, with the use of [$^3$H] flumazenil in place of [$^3$H] diazepam as radioligand.

The tissue of the cerebellum is homogenized for 60 s in 120 volumes of ice-cold buffer (50 mM of Tris/HCl, pH 7.4, 120 mM NaCl, 5 mM KCl) and then, after dilution to ⅓, the suspension is incubated with [$^3$H] flumazenil (specific activity: 78 Ci/mmol; New England Nuclear) at a concentration of 1 nM and with the compounds of the invention, at different concentrations, in a final volume of 525 μl. After incubating for 30 min at 0° C., the samples are filtered under vacuum on Whatman GF/B™ filters and they are washed immediately with ice-cold buffer. The specific binding of [$^3$H] flumazenil is determined in the presence of 1 μM unlabelled diazepam. The data are analysed according to the usual methods and the IC$_{50}$, the concentration which inhibits 50% of the binding of [$^3$H] flumazenil, is calculated.

The IC$_{50}$ values of the compounds of the invention lie, in this test, between 0.1 and 10 μM.

The results of the tests carried out on the compounds of the invention show that, in vitro, they selectively displace [$^3$H] flumazenil from its membrane binding sites with respect to a population of ω receptors (benzodiazepine receptors) associated with GABA$_A$ receptors containing the α$_5$ subunit, in comparison with ω$_1$-receptor subtypes associated with GABA$_A$ receptors containing the α$_1$ unit, and in comparison with a population of ω$_2$ receptors (type-II benzodiazepine receptors) associated with GABA$_A$ receptors containing mostly the α$_2$ and α$_3$ subunits.

In other words, the compounds have an affinity which is high for the membrane binding sites of [$^3$H] flumazenil with respect to a population of ω receptors (benzodiazepine receptors) associated with GABA$_A$ receptors containing the α$_5$ subunit, moderate or low for the ω$_1$-receptor (type-I benzodiazepine receptor) subtypes associated with GABA$_A$ receptors containing the α$_1$ subunit, moderate or low for a population of ω$_2$ receptors (type-II benzodiazepine receptors) associated with GABA$_A$ receptors containing mostly the α$_2$ and α$_3$ subunits.

The selectivity represented by the ω$_1$-cerebellum IC$_{50}$/ω-hippocampus IC$_{50}$ ratio is between 5 and 25 and that represented by the ω$_2$-spinal cord IC$_{50}$/ω-hippocampus IC$_{50}$ ratio is also between 5 and 25.

The compounds of the invention can be used in the treatment of ailments related to disorders of GABAergic transmission of GABA$_A$ receptors associated with the α$_5$ subunit. The preferential distribution of the ω receptors, associated with the α$_5$ subunit of the GABA$_A$ receptor complex, in the olfactory bulb, in limbic structures, such as the hippocampus and the hypothalamus, and in the spinal cord, suggest that the compounds of the invention can be used in the treatment of disorders of olfaction, cognitive disorders, hormonal disorders related to dysfunctioning of the hypothalamus, certain emotional disorders and perception of pain. They can also be used in the treatment of spasticity and cramps.

The present invention also provides a pharmaceutical composition comprising a compound of formula (I) and an excipient, for enteral or parenteral administration, for example in the form of a tablet, dragée, gelatin capsule, capsule, solution or suspension to be taken orally or to be injected, or suppository, containing doses which make possible the daily administration of 1 to 1000 mg of active substance.

The present invention also provides a compound of formula (I) for use in a method of treatment of the human or animal body.

The present invention further provides the use of a compound of formula (I) in the manufacture of a medicament for use in the treatment of an ailment related to a disorder of the GABAergic transmission of GABA$_A$ receptors associated with the α$_5$ subunit.

There is also disclosed a method of treatment of a subject suffering from an ailment related to a disorder of the GABAergic transmission of GABA$_A$ receptors associated with the $\alpha_5$ subunit which comprises administering to that subject an effective amount of a compound of formula (I).

The present invention also provides a composition for the treatment of an ailment related to a disorder of the GABAergic transmission of GABA$_A$ receptors associated with the $\alpha_5$ subunit which comprises a compound of formula (I) and a pharmaceutically acceptable adjuvant.

We claim:

1. A compound of formula (I)

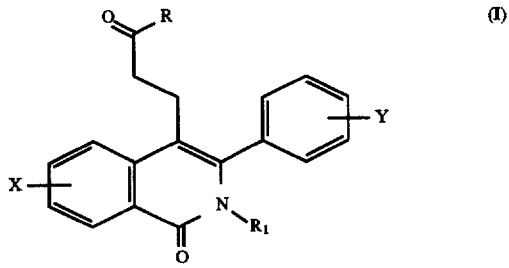

in which

X represents a hydrogen atom, a halogen atom, a trifluoromethyl group, a $C_1$–$C_3$ alkyl group or a $C_1$–$C_3$ alkoxy group in which case two such alkoxy groups X can be present, Y represents a hydrogen atom, a halogen atom, a $C_1$–$C_3$ alkyl group or a $C_1$–$C_3$ alkoxy group, R$_1$ represents a $C_1$–$C_4$ alkyl group, and R represents a hydroxyl group, a methoxy group, an ethoxy group or a group of formula NR$_2$R$_3$ in which R$_2$ and R$_3$ each independently represents a hydrogen atom or a $C_1$–$C_4$ alkyl group, or a pharmaceutically acceptable addition salt thereof.

2. A compound according to claim 1, in which R$_1$ represents a methyl group and R represents a methylamino group.

3. A compound of formula (I) selected from the group consisting of 2-methyl-1-oxo-3-phenyl-1,2-dihydroisoquinoline-4-propanoic acid, methyl 2-methyl-1-oxo-3-phenyl-1,2-dihydroisoquinoline-4-propionate, ethyl 2-methyl-1-oxo-3-phenyl-1,2-dihydroisoquinoline-4-propanoate, N,2-dimethyl-1-oxo-3-phenyl-1,2-dihydroisoquinoline-4-propanamide, N,2-dimethyl-5-methoxy-1-oxo-3-phenyl-1,2-dihydroisoquinoline-4-propanamide, N,2,6-trimethyl-1-oxo-3-phenyl-1,2-dihydroisoquinoline-4-propanamide, 6-chloro-N,2-dimethyl-1-oxo-3-phenyl-1,2-dihydroisoquinoline-4-propanamide, 6-methoxy-N,2-dimethyl-1-oxo-3-phenyl-1,2-dihydroisoquinoline-4-propanamide, N,2,7-trimethyl-1-oxo-3-phenyl-1,2-dihydroisoquinoline-4-propanamide, 7-chloro-N,2-dimethyl-1-oxo-3-phenyl-1,2-dihydroisoquinoline-4-propanamide, N-butyl-7-chloro-2-methyl-1-oxo-3-phenyl-1,2-dihydroisoquinoline-4-propanamide, 7-methoxy-N,2-dimethyl-1-oxo-3-phenyl-1,2-dihydroisoquinoline-4-propanamide, N,2-dimethyl-1-oxo-3-phenyl-7-trifluoromethyl-1,2-dihydroisoquinoline-4-propanamide, 8-methoxy-N,2-dimethyl-8-methoxy-1-oxo-3-phenyl-1,2-dihydroisoquinoline-4-propanamide, 6,7-dimethoxy-N,2-dimethyl-1-oxo-3-phenyl-1,2-dihydroisoquinoline-4-propanamide, N,2-dimethyl-1-oxo-3-(3-methylphenyl)-1,2-dihydroisoquinoline-4-propanamide, N,2-dimethyl-1-oxo-3-(3-methoxyphenyl)-1,2-dihydroisoquinoline-4-propanamide, N,2-dimethyl-1-oxo-3-(3-chlorophenyl)-1,2-dihydroisoquinoline-4-propanamide, N,2-dimethyl-1-oxo-3-(4-fluorophenyl)-1,2-dihydroisoquinoline-4-propanamide, N,2-dimethyl-1-oxo-3-(4-chlorophenyl)-1,2-dihydroisoquinoline-4-propanamide, N,2,7-trimethyl-1-oxo-3-(3-chlorophenyl)-1,2-dihydroisoquinoline-4-propanamide, N,2,7-trimethyl-1-oxo-3-(3-fluorophenyl)-1,2-dihydroisoquinoline-4-propanamide, N,N,2-trimethyl-1-oxo-3-phenyl-1,2-dihydroisoquinoline-4-propanamide, 7-chloro-N,N-diethyl-2-methyl-1-oxo-3-phenyl-1,2-dihydroisoquinoline-4-propanamide, 2-ethyl-1-oxo-3-phenyl-1,2-dihydroisoquinoline-4-propanoic acid, 2-ethyl-N-methyl-1-oxo-3-phenyl-1,2-dihydroisoquinoline-4-propanamide, 2-ethyl-N,N-dimethyl-1-oxo-3-phenyl-1,2-dihydroisoquinoline-4-propanamide 2-propyl-N-methyl-1-oxo-3-phenyl-1,2-dihydroisoquinoline-4-propanamide and pharmaceutically acceptable addition salts thereof.

4. Process for the preparation of a compound according to claim 1, in which a 3-phenylisoquinol-1(2 H)-one of formula (II)

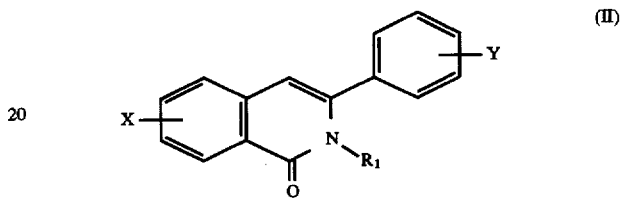

in which X, Y, and R$_1$ are as defined in claim 1, is treated with phosphorus oxychloride to obtain an aldehyde of formula (III)

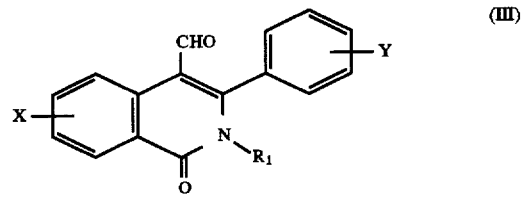

which is then treated with methyl (dimethoxyphosphinyl)acetate to obtain a methyl ester of formula (IV)

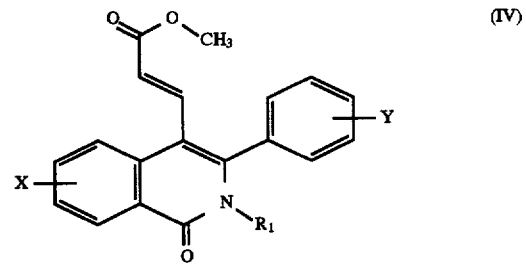

which is then hydrogenated to obtain an ester of formula (Ia)

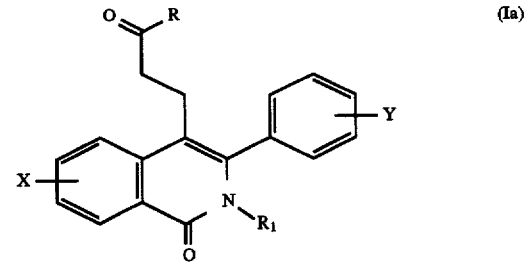

which corresponds to a compound of formula (I) in which R represents a methoxy group, then, if a compound of formula (I) in which R represents a hydroxyl group is desired, the ester of formula (Ia) is hydrolysed to obtain a compound of formula (Ib)

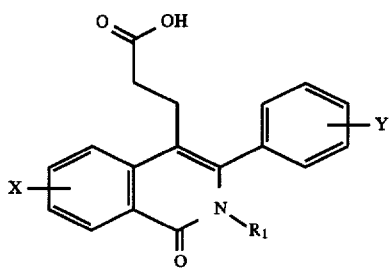 (Ib)

and, if a compound of formula (I) in which R represents a group of formula $NR_2R_3$ is desired, either the ester of formula (Ia) is treated with an amine of formula $HNR_2R_3$, or the acid of formula (Ib) is treated with the amine of formula $HNR_2R_3$ and N,N-carbonyldiimidazole, and, if a compound of formula (I) in which R represents an ethoxy group is desired, the acid of general formula (Ib) is reacted with thionyl chloride in ethanol, and, if desired, the compound of formula (I) is converted into an addition salt thereof.

5. A compound of formula (I), prepared by the process of claim 4.

6. Pharmaceutical composition, which comprises a compound according to claim 1 and an excipient.

7. A method of treatment of a subject suffering from an ailment related to a disorder of the GABAergic transmission of $GABA_A$ receptors associated with the $\alpha_5$ subunit which comprises administering to that subject an effective amount of a compound according to claim 1.

* * * * *